US012651660B1

(12) United States Patent
Archibald et al.

(10) Patent No.: US 12,651,660 B1
(45) Date of Patent: Jun. 9, 2026

(54) APPARATUS AND METHOD FOR PEPTIDE STACK DETERMINATION

(71) Applicant: Ageless Medicine Systems LLC, Midvale, UT (US)

(72) Inventors: Cade Archibald, Midvale, UT (US); Regan Archibald, Midvale, UT (US)

(73) Assignee: Ageless Medicine Systems LLC, Midvale, UT (US)

( * ) Notice: Subject to any disclaimer, the term of this patent is extended or adjusted under 35 U.S.C. 154(b) by 0 days.

(21) Appl. No.: 18/975,735

(22) Filed: Dec. 10, 2024

(51) Int. Cl.
  G16H 20/10 (2018.01)
  G16H 50/50 (2018.01)
  G06F 40/40 (2020.01)

(52) U.S. Cl.
  CPC ............. G16H 20/10 (2018.01); G16H 50/50 (2018.01); G06F 40/40 (2020.01)

(58) Field of Classification Search
  None
  See application file for complete search history.

(56) References Cited

U.S. PATENT DOCUMENTS

| | | | |
|---|---|---|---|
| 10,213,473 B2 | 2/2019 | Lied et al. | |
| 2023/0268053 A1 | 8/2023 | Nagendra | |

| | | | |
|---|---|---|---|
| 2024/0194340 A1 | 6/2024 | Neumann | |
| 2024/0363213 A1 * | 10/2024 | Rocco .................... | G16H 10/20 |
| 2025/0277209 A1 * | 9/2025 | Szablowski ........ | C12N 15/1082 |

FOREIGN PATENT DOCUMENTS

| | | |
|---|---|---|
| WO | 2024107754 A1 | 5/2024 |

OTHER PUBLICATIONS

Peptides; Peter M. D website.
What Are Peptides? Find Out the Best Peptide Stacks; bengreenfieldlife website Dec. 18, 2023.
Peptide Therapy; VYVE Wellness website.

* cited by examiner

*Primary Examiner* — Joseph D Burgess
(74) *Attorney, Agent, or Firm* — CALDWELL LLC

(57) ABSTRACT

Apparatus and method for peptide stack determination are disclosed. The apparatus includes a memory containing instructions configuring at least a processor to receive subject data, retrieve peptide data, convert the peptide data into a machine-readable input, generate a peptide stack datum as a function of the subject data and the machine-readable input and determining the peptide stack datum includes generating stack training data, wherein the stack training data includes exemplary subject data and exemplary machine-readable inputs correlated to exemplary peptide stack datums, training a stack machine-learning model trained with the stack training data and generating the peptide stack datum using the trained stack machine-learning model and generate a user interface displaying the peptide stack datum on a remote device.

16 Claims, 9 Drawing Sheets

180

132

164 — Target: Boost Energy and Improve Metabolism

116 — Peptide Stack 1

Peptide A + Peptide B
Ratio: 1:2

Peptide Stack 2

200 — Peptide A + Peptide C
Ratio: 1:3

Peptide Stack 3

120 — Peptide B + Peptide D + Peptide E
Ratio: 2:2:1

184

| Target | Patient Medical Condition | Peptide Stack |
|--------|---------------------------|---------------|
| 164 | 124 | 116 |
| Energy Boost & Anti-aging | Condition 1, Condition 2 and Condition 3 | Peptide A + Peptide B |
| Muscle Growth & Anti-aging | Condition 1, Condition 2 and Condition 3 | Peptide A + Peptide C |
| Fat Loss & Immune Enhancement | Condition 1, Condition 2 and Condition 3 | Peptide A + Peptide C + Peptide D |
| • • • | • • • | • • • |
| • • • | • • • | • • • |

FIG. 7

APPARATUS AND METHOD FOR PEPTIDE STACK DETERMINATION

FIELD OF THE INVENTION

The present invention generally relates to the field of biotechnology and artificial intelligence. In particular, the present invention is directed to an apparatus and method for peptide stack determination.

BACKGROUND

Health metrics and other relevant data can change daily, influenced by various factors. Existing systems for managing and generating data related to patients and peptides are limited in their ability to handle and process this continuously evolving data efficiently. These systems often lack real-time monitoring capabilities and cannot dynamically adjust treatment protocols based on immediate changes in patient data.

SUMMARY OF THE DISCLOSURE

In an aspect, an apparatus for peptide stack determination is disclosed. The apparatus includes at least a processor and a memory communicatively connected to the at least a processor, wherein the memory contains instructions configuring the at least a processor to receive subject data, wherein the subject data includes user condition data and a peptide request datum, retrieve peptide data from a peptide database, wherein the peptide data includes information related to a plurality of peptides, convert the peptide data into a machine-readable input, generate a peptide stack datum as a function of the subject data and the machine-readable input, wherein the peptide stack datum is related to a combination of at least two peptides of the plurality of peptides that are compatible to the user condition data and determining the peptide stack datum includes generating stack training data, wherein the stack training data includes exemplary subject data and exemplary machine-readable inputs correlated to exemplary peptide stack datums, training a stack machine-learning model trained with the stack training data and generating the peptide stack datum using the trained stack machine-learning model and generate a user interface displaying the peptide stack datum on a remote device.

In another aspect, a method for peptide stack determination is disclosed. The method includes receiving, using at least a processor, subject data, wherein the subject data includes user condition data and a peptide request datum, retrieving, using the at least a processor, peptide data from a peptide database, wherein the peptide data includes information related to a plurality of peptides, converting, using the at least a processor, the peptide data into a machine-readable input, generating, using the at least a processor, a peptide stack datum as a function of the subject data and the machine-readable input, wherein the peptide stack datum is related to a combination of at least two peptides of the plurality of peptides that are compatible to the user condition data and determining the peptide stack datum includes generating stack training data, wherein the stack training data comprises exemplary subject data and exemplary machine-readable inputs correlated to exemplary peptide stack datums, training a stack machine-learning model trained with the stack training data and generating the peptide stack datum using the trained stack machine-learning model and generating, using the at least a processor, a user interface displaying the peptide stack datum on a remote device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 7 illustrates an exemplary categorized database;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatuses and methods for peptide stack determination is disclosed. The apparatus includes at least a processor and a memory communicatively connected to the at least a processor, wherein the memory contains instructions configuring the at least a processor to receive subject data, wherein the subject data includes user condition data and a peptide request datum, retrieve peptide data from a peptide database, wherein the peptide data includes information related to a plurality of peptides, convert the peptide data into a machine-readable input, generate a peptide stack datum as a function of the subject data and the machine-readable input, wherein the peptide stack datum is related to a combination of at least two peptides of the plurality of peptides that are compatible to the user condition data and determining the peptide stack datum includes generating stack training data, wherein the stack training data includes exemplary subject data and exemplary machine-readable inputs correlated to exemplary peptide stack datums, training a stack machine-learning model trained with the stack training data and generating the peptide stack datum using the trained stack machine-learning model and generate a user interface displaying the peptide stack datum on a remote device. Exemplary embodiments illustrating aspects of the present disclosure are described below in the context of several specific examples.

Figure 1:
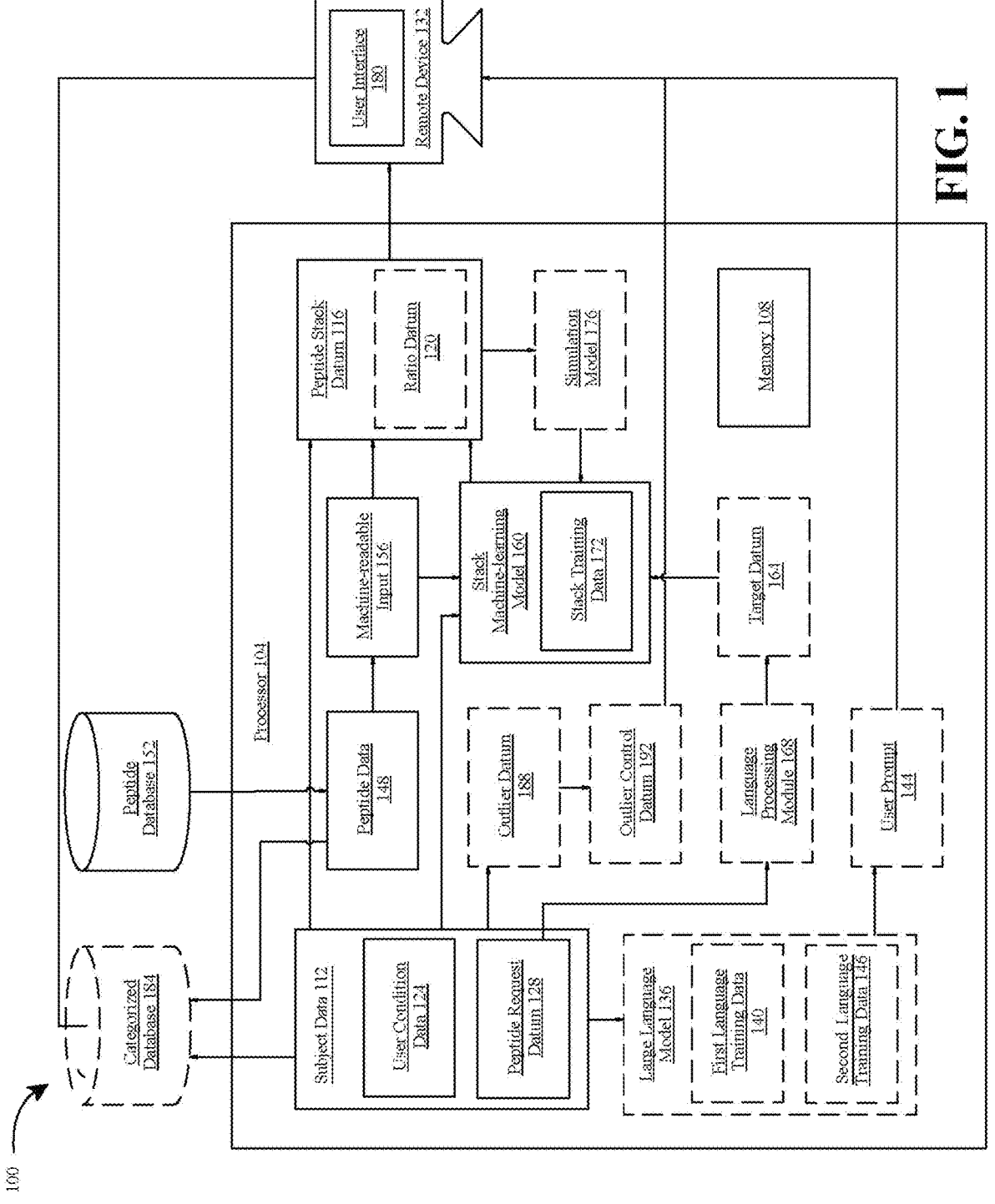
FIG. 1 illustrates a block diagram of an exemplary apparatus for peptide stack determination.

Referring now to FIG. 1, an exemplary embodiment of an apparatus 100 for peptide stack determination is illustrated. Apparatus 100 includes at least a processor 104. Processor 104 may include, without limitation, any processor described in this disclosure. Processor 104 may be included in a computing device. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 104. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 contains instructions configuring processor 104 to receive subject data 112. For the purposes of this disclosure, "subject data" is data related to a user. For the purposes of this disclosure, a "user" is any person or individual that is using or has used an apparatus. As a non-limiting example, user may include a patient. As a non-limiting example, subject data 112 may include demographic information such as age, gender, ethnicity, medical history, and the like. As another non-limiting example, subject data 112 may include information related to chronic conditions like diabetes, hypertension, cardiovascular diseases, and autoimmune disorders, as well as medical events such as surgeries, hospitalizations, and treatments. As another non-limiting example, subject data 112 may include information about current and past medications, including dosages and duration of use. As another non-limiting example, subject data 112 may include genetic information, which includes deoxyribonucleic acid (DNA) data obtained from genetic tests, family history of prevalent health conditions, and the like. As another non-limiting example, subject data 112 may include lifestyle information, encompassing diet, exercise, sleep patterns, and habits like smoking and alcohol consumption. In some embodiments, subject data 112 may include user preferences regarding peptide stack datum 116, such as preferred administration methods (e.g., oral, injectable), dosage preferences, any known allergies or intolerances to specific peptides, any constraints, such as budgetary limits or timing considerations, and the like. In some embodiments, processor 104 may determine peptide stack datum 116 or ratio datum 120 or dosage datum as a function of user preferences.

With continued reference to FIG. 1, subject data 112 includes user condition data 124. For the purposes of this disclosure, "user condition data" is data related to a user's health condition. As a non-limiting example, user condition data 124 may include glucose levels, inflammatory markers, microbiome composition, and the like. As another non-limiting example, user condition data 124 may include health metrics like blood pressure, heart rate, body temperature, and respiratory rate. As another non-limiting example, user condition data 124 may include body measurements, including weight, height, body mass index (BMI), and body composition metrics such as fat percentage and muscle mass. As another non-limiting example, user condition data 124 may include biomarker data derived from blood, urine, stool, microbiota and DNA tests provides detailed information about levels of glucose, cholesterol, triglycerides, hormones, vitamins, inflammatory markers, and the microbiome composition. As another non-limiting example, user condition data 124 may include data collected through health questionnaires or surveys, as well as data from wearable devices or health apps.

With continued reference to FIG. 1, subject data 112 includes a peptide request datum 128. For the purposes of this disclosure, a "peptide request datum" is a data element related to a request for a peptide stack aimed at achieving a particular health-related goal or target. In some embodiments, a third party may input peptide request datum 128. For the purposes of this disclosure, a "third party" is any individual or organization that is not a user. As a non-limiting example, third party may include a health care worker, doctor, health care organization, and the like. In a non-limiting example, peptide request datum 128 may be 'give me a peptide stack that can boost energy and enhance muscle growth.' In some embodiments, peptide request datum 128 may include a peptide target. For the purposes of this disclosure, a "peptide target" is a target or goal that a user aims to achieve with a peptide stack. As a non-limiting example, peptide request datum 128 may include goals such as boosting energy, enhancing muscle growth, promoting fat loss, improving cognitive function, enhancing immune response, or achieving specific therapeutic effects.

With continued reference to FIG. 1, processor 104 may receive subject data 112 using an application programming interface (API). As used in the current disclosure, an "application programming interface" is a software interface for two or more computer programs to communicate with each other. As a non-limiting example, API may include electronic health record (HER) APIs, telemedicine APIs, and the like. For the purposes of this disclosure, an "electronic health record" is the systematized collection of patient and population electronically stored health information in a digital format. An application programming interface may be a type of software interface, offering a service to other pieces of software. In contrast to a user interface, which connects a computer to a person, an application programming interface may connect computers or pieces of software to each other. An API may not be intended to be used directly by a person (e.g., a user or third party) other than a computer programmer who is incorporating it into the software. An API may be made up of different parts which act as tools or services that are available to the programmer. A program or a programmer that uses one of these parts is said to call that portion of the API. The calls that make up the API are also known as subroutines, methods, requests, or endpoints. An API specification may define these calls, meaning that it explains how to use or implement them. One purpose of API may be to hide the internal details of how a system works, exposing only those parts a programmer will find useful and keeping them consistent even if the internal details later change. An API may be custom-built for a particular pair of systems, or it may be a shared standard allowing interoperability among many systems. The term API may be often used to refer to web APIs, which allow communication between computers that are joined by the internet. API may be configured to query for web applications in order to retrieve subject data 112 to another web application, database (e.g., subject database), medical center patient portal, and the like. An API may be further configured to filter through web applications according to a filter criterion. In this disclosure, "filter criteria" are conditions the web applications must fulfill in order to qualify for API. Web applications may be filtered based on these filter criteria. Filter criteria may include, without limitation, types of medical facilities, location of the medical facility, and the like.

With continued reference to FIG. 1, in some embodiments, processor 104 may receive subject data 112 from remote device 132. For the purposes of this disclosure, a "remote device" is any device a user or third party uses to input data. As a non-limiting example, remote device 132 may include a laptop, desktop, tablet, mobile phone, smart phone, smart watch, kiosk, screen, smart headset, or things of the like. In some embodiments, remote device 132 may include an interface configured to receive inputs from a user or third party. In some embodiments, user or third party may manually input any data into apparatus 100 using remote device 132. In some embodiments, user or third party may have a capability to process, store or transmit any information independently.

With continued reference to FIG. 1, in some embodiments, processor 104 may receive subject data 112 from a wearable device. A "wearable device," as used in this disclosure, is a device on a user that collects subject data, where "on the user" indicates that the device is portable and is either worn on the user, inside the user, in contact with the user, or in close proximity to the user. Subject data 112 may include data generated, collected, and/or transmitted by the wearable device and may include wearables worn by user such as an accelerometer, pedometer, gyroscope, fitness trackers, force monitors, motion sensors; wearables in contact with a user's skin such as in electrocardiography (ECG), electrooculography (EOG), bioimpedance, blood pressure and heart rate monitoring, oxygenation data, biosensors, eye tracking system; wearables that may be placed inside and/or within a user, and/or devices that may be adapted to be placed outside of user but aimed at collecting data pertaining to user, such as audio-visual capture, social media platform data, facial recognition, and the like. Wearable devices may be any devices capably and useful in acquiring, measuring, and/or transmitting subject data 112—body measurements and calculates related to human characteristics. Subject data 112 may include any data that is useful in biometrically identifying a user, including fingerprints, retina scans, genetic material data, physical appearance, voice recognition, or any other data useful in identifying an individual.

With continued reference to FIG. 1, in some embodiments, apparatus 100 may include a subject database. As used in this disclosure, "subject database" is a data structure configured to store data associated with user. As a non-limiting example, subject database may store subject data 112, user condition data 124, and the like. In one or more embodiments, subject database may include inputted or calculated information and datum related to a user. In some embodiments, a datum history may be stored in subject database. As a non-limiting example, the datum history may include real-time and/or previous inputted data related to user. As a non-limiting example, subject database may include instructions from a user, who may be an expert user, a past user in embodiments disclosed herein, or the like, where the instructions may include examples of subject data 112.

With continued reference to FIG. 1, in some embodiments, processor 104 may be communicatively connected with subject database. For example, and without limitation, in some cases, subject database may be local to processor 104. In another example, and without limitation, subject database may be remote to processor 104 and communicative with processor 104 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infra-structure processor 104 connect directly, dynamically, and non-hierarchically to as many other computing devices as possible. A "network topology" as used in this disclosure is an arrangement of elements of a communication network. The network may use an immutable sequential listing to securely store subject database. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in some embodiments, subject database may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in some embodiments, processor 104 may receive subject data 112 from a chatbot or virtual assistant. For the purposes of this disclosure, "chatbot" is an artificial intelligence (AI) program designed to simulate human conversation or interaction through text, voice-based or image-based communication. The chatbot disclosed herein is further described below. For the purposes of this disclosure, a "virtual assistant" is a software designed to interact with users through natural language processing (NLP) to collect, manage, and process information provided by the users. In some embodiments, receiving subject data 112 may include training a large language model (LLM) 136 with a first language training set 140 and generating a user prompt 144 using the large language model 136. In some embodiments, a first language training set 140 may include exemplary subject data correlated to exemplary user prompts. For the purposes of this disclosure, a "user prompt" is a question or statement to elicit subject data from a user. For instance, user prompt 144 may include "Please enter your weight in pounds." In some embodiments, large language model 136 may be further trained with a second language training set 146. In some embodiments, second language training set 146 may include interactions of users of different language skills and education levels. In some embodiments, LLM 136 may be trained on diverse datasets (second language training set 146) that include interactions with users of different language skills. As a non-limiting example, LLM 136 may recognize cues from the user's input, such as vocabulary, sentence structure, and grammar, to gauge their language proficiency. For example, and without limitation, is a user demonstrates limited vocabulary and simpler sentence constructions, LLM 136 may simplify its responses and explanations. In some embodiments, LLM 136 may be trained to adjust its language based on the inferred or explicitly provided education level of a user. As a non-limiting example, this may include rephrasing technical or specialized terms into more common language that is easier to understand for users with lower education levels. For example, and without limitation, for a user with a high school education, LLM 136 may explain "hypertension" as "high blood pressure," whereas for a user with medical training, LLM 136 may use the term "hypertension."

With continued reference to FIG. 1, a "large language model," as used herein, is a deep learning data structure that can recognize, summarize, translate, predict and/or generate text and other content based on knowledge gained from massive datasets. Large language model 136 may be trained on large sets of data. Training sets may be drawn from diverse sets of data such as, as non-limiting examples, EHR, telemedicine communication, research paper, survey, and the like. In some embodiments, training sets may include a variety of subject matters, such as, as nonlimiting examples, user's health, medical knowledge, and the like. In some embodiments, training sets of an LLM 136 may include information from one or more public or private databases. As a non-limiting example, training sets may include databases associated with a user (e.g., subject database). In some embodiments, training sets may include portions of documents associated with subject data 112 correlated to examples of outputs. In an embodiment, an LLM 136 may include one or more architectures based on capability requirements of an LLM 136. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM 136 may be generally trained. As used in this disclosure, a "generally trained" LLM is an LLM that is trained on a general training set comprising a variety of subject matters, data sets, and fields. In some embodiments, an LLM 136 may be initially generally trained. In a non-limiting example, LLM 136 may be generally trained using a first language training set 140. Additionally, or alternatively, an LLM 136 may be specifically trained. As used in this disclosure, a "specifically trained" LLM is an LLM that is trained on a specific training set, wherein the specific training set includes data including specific correlations for the LLM to learn. As a non-limiting example, an LLM 136 may be generally trained on a general training set (e.g., first language training set 140), then specifically trained on a specific training set (e.g., second language training set 146). In an embodiment, specific training of an LLM 136 may be performed using a supervised machine-learning process. In some embodiments, generally training an LLM 136 may be performed using an unsupervised machine-learning process. As a non-limiting example, specific training set may include information from a database. As a non-limiting example, specific training set may include text related to the users such as user specific data for electronic records correlated to examples of outputs. In an embodiment, training one or more machine-learning models may include setting the parameters of the one or more models (weights and biases) either randomly or using a pretrained model. Generally training one or more machine-learning models on a large corpus of text data can provide a starting point for fine-tuning on a specific task. A model such as an LLM 136 may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyper-parameters such as learning rate, batch size, and regularization. Hyperparameter tuning may help in achieving the best performance and convergence during training. In an embodiment, fine-tuning a pretrained model such as an LLM 136 may include fine-tuning the pretrained model using Low-Rank Adaptation (LoRA). As used in this disclosure, "Low-Rank Adaptation" is a training technique for large language model 136 that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM 136 may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM 136 may include a text prediction based algorithm configured to receive an article and apply a probability distribution to the words already typed in a sentence to work out the most likely word to come next in augmented articles. For example, if some words that have already been typed are "Nice to meet," then it may be highly likely that the word "you" will come next. An LLM 136 may output such predictions by ranking words by likelihood or a prompt parameter. For the example given above, an LLM 136 may score "you" as the most likely, "your" as the next most likely, "his" or "her" next, and the like. An LLM 136 may include an encoder component and a decoder component.

With continued reference to FIG. 1, an LLM 136 may include a transformer architecture. In some embodiments, encoder component of an LLM 136 may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM 136 and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM 136 may predict the next word by searching for a set of positions in a source sentence where the most relevant information is concentrated. An LLM 136 may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

With continued reference to FIG. 1, attention mechanism may include, without limitation, generalized attention self-attention, multi-head attention, additive attention, global attention, and the like. In generalized attention, when a sequence of words or an image is fed to an LLM 136, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM 136 may pick up particular parts at different positions in the input sequence and over time compute an initial composition of the output sequence. In multi-head attention, an LLM 136 may include a transformer model of an attention mechanism. Attention mechanisms, as described above, may provide context for any position in the input sequence. For example, if the input data is a natural language sentence, the transformer does not have to process one word at a time. In multi-head attention, computations by an LLM 136 may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM 136 may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM 136 may either attend to all source words or predict the target sentence, thereby attending to a smaller subset of words.

With continued reference to FIG. 1, multi-headed attention in encoder may apply a specific attention mechanism called self-attention. Self-attention allows models such as an LLM 136 or components thereof to associate each word in the input, to other words. As a non-limiting example, an LLM 136 may learn to associate the word "you", with "how" and "are". It's also possible that an LLM 136 learns that words structured in this pattern are typically a question and to respond appropriately. In some embodiments, to achieve self-attention, input may be fed into three distinct fully connected neural network layers to create query, key, and value vectors. A query vector may include an entity's learned representation for comparison to determine attention score. A key vector may include an entity's learned representation for determining the entity's relevance and attention weight. A value vector may include data used to generate output representations. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

With continued reference to FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

With continued reference to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "Os" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

With continued reference to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

With continued reference to FIG. 1, decoder may take this output and add it to the decoder inputs. Decoder may continue decoding until a token is predicted. Decoder may stop decoding once it predicts an end token.

With continued reference to FIG. 1, in some embodiment, decoder may be stacked N layers high, with each layer taking in inputs from the encoder and layers before it. Stacking layers may allow an LLM 136 to learn to extract and focus on different combinations of attention from its attention heads.

With continued reference to FIG. 1, an LLM 136 may receive an input. Input may include a string of one or more characters. Inputs may additionally include unstructured data. For example, input may include one or more words, a sentence, a paragraph, a thought, a query, and the like. For example, input may include subject data 112, user condition data 124, peptide request datum 128, and the like. For example, input may include user's question. A "query" for the purposes of the disclosure is a string of characters that poses a question. In some embodiments, input may be received from a remote device 132. Remote device 132 may be any computing device that is used by a user or third party. As non-limiting examples, remote device 132 may include desktops, laptops, smartphones, tablets, and the like. In some embodiments, input may include any set of data associated with subject data 112, user condition data 124, peptide request datum 128, and the like.

With continued reference to FIG. 1, an LLM 136 may generate user prompt 144 as an output. In some embodiments, an LLM 136 may include multiple sets of transformer architecture as described above. Output may include a textual output. A "textual output," for the purposes of this disclosure is an output comprising a string of one or more characters. Textual output may include, for example, user prompt 144 to receive more subject data 112 from user. Textual output may include, for example, a response to a user's question. In some embodiments, textual output may include a sentence or plurality of sentences describing a response to a user query.

With continued reference to FIG. 1, in some embodiments, receiving subject data 112 may include converting subject data 112 in an audio format into a textual format. In some embodiments, processor 104 may receive subject data 112 (e.g., user condition data 124 or peptide request datum 128) in audio format from remote device 132. In some embodiments, processor 104 may retrieve subject data 112 in audio format from subject database.

With continued reference to FIG. 1, in some embodiments, processor 104 may convert subject data 112 in audio format to subject data 112 in textual format using automatic speech recognition (ASR). Subject data 112 in textual format may be a written representation of spoken words, phrases, and other relevant audio elements of subject data 112 in audio format. As a non-limiting example, ASR may analyze a record of a call or video call or audio chat to obtain subject data 112 in audio format. For the purposes of this disclosure, "automatic speech recognition" is a technology that converts spoken language into written text or machine-readable form. In a non-limiting example, processor 104 may use a record of a call or video call between user and third party to aid in recognition of subject data 112 in audio format. In some embodiments, ASR may include techniques employing language processing to aid speech recognition processes. In some cases, ASR may be used to decode (i.e., recognize) indeterministic phonemes or help in forming a preponderance among probabilistic candidates. In some cases, ASR may include an audio-based automatic speech recognition process and an image-based automatic speech recognition process. ASR may analysis audio according to any method described herein, for instance using a Mel frequency cepstral coefficients (MFCCs) and/or log-Mel spectrogram derived from raw audio samples. In some cases, feature recognition may include any feature recognition process described in this disclosure, for example a variant of a convolutional neural network. For instance, audio vector may each be concatenated and used to predict speech made by data provider of user.

With continued reference to FIG. 1, in some embodiments, automatic speech recognition may require training (i.e., enrollment). In some cases, training an automatic speech recognition model may require an individual speaker to read text or isolated vocabulary. In some cases, a solicitation video may include an audio component having subject data 112 in audio format, the contents of which are known a priori by processor 104. Processor 104 may then train an automatic speech recognition model according to training data which includes subject data 112 in audio format correlated to known content (e.g., subject data 112 in textual format). In this way, processor 104 may analyze a person's specific voice and train an automatic speech recognition model to the person's speech, resulting in increased accuracy. Alternatively or additionally, in some cases, processor 104 may include an automatic speech recognition model that is speaker-independent. As used in this disclosure, a "speaker independent" automatic speech recognition process does not require training for each individual speaker. Conversely, as used in this disclosure, automatic speech recognition processes that employ individual speaker specific training are "speaker dependent."

With continued reference to FIG. 1, in some embodiments, an automatic speech recognition process may perform voice recognition or speaker identification. As used in this disclosure, "voice recognition" refers to identifying a speaker, from audio content, rather than what the speaker is saying. In some cases, processor 104 may first recognize a speaker of subject data 112 in audio format and then automatically recognize speech of the speaker, for example by way of a speaker dependent automatic speech recognition model or process. In some embodiments, an automatic speech recognition process can be used to authenticate or verify an identity of a speaker. In some cases, a speaker may or may not include subject. For example, subject may speak within solicitation video, but others may speak as well.

With continued reference to FIG. 1, in some embodiments, an automatic speech recognition process may include one or all of acoustic modeling, language modeling, and statistically-based speech recognition algorithms. In some cases, an automatic speech recognition process may employ hidden Markov models (HMMs). As discussed in greater detail below, language modeling such as that employed in natural language processing applications like document classification or statistical machine translation, may also be employed by an automatic speech recognition process.

With continued reference to FIG. 1, an exemplary algorithm employed in automatic speech recognition may include or even be based upon hidden Markov models. Hidden Markov models (HMMs) may include statistical models that output a sequence of symbols or quantities. HMMs can be used in speech recognition because a speech signal can be viewed as a piecewise stationary signal or a short-time stationary signal. For example, over a short time scale (e.g., 10 milliseconds), speech can be approximated as a stationary process. Speech (i.e., subject data 112 in audio format) can be understood as a Markov model for many stochastic purposes.

With continued reference to FIG. 1, in some embodiments HMMs can be trained automatically and may be relatively simple and computationally feasible to use. In an exemplary automatic speech recognition process, a hidden Markov model may output a sequence of n-dimensional real-valued vectors (with n being a small integer, such as 10), at a rate of about one vector every 10 milliseconds. Vectors may consist of cepstral coefficients. A cepstral coefficient requires using a spectral domain. Cepstral coefficients may be obtained by taking a Fourier transform of a short time window of speech yielding a spectrum, decorrelating the spectrum using a cosine transform, and taking first (i.e., most significant) coefficients. In some cases, an HMM may have in each state a statistical distribution that is a mixture of diagonal covariance Gaussians, yielding a likelihood for each observed vector. In some cases, each word, or phoneme, may have a different output distribution; an HMM for a sequence of words or phonemes may be made by concatenating an HMMs for separate words and phonemes.

With continued reference to FIG. 1, in some embodiments, an automatic speech recognition process may use various combinations of a number of techniques in order to improve results. In some cases, a large-vocabulary automatic speech recognition process may include context dependency for phonemes. For example, in some cases, phonemes with different left and right context may have different realizations as HMM states. In some cases, an automatic speech recognition process may use cepstral normalization to normalize for different speakers and recording conditions. In some cases, an automatic speech recognition process may use vocal tract length normalization (VTLN) for male-female normalization and maximum likelihood linear regression (MLLR) for more general speaker adaptation. In some cases, an automatic speech recognition process may determine so-called delta and delta-delta coefficients to capture speech dynamics and might use heteroscedastic linear discriminant analysis (HLDA). In some cases, an automatic speech recognition process may use splicing and a linear discriminate analysis (LDA)-based projection, which may include heteroscedastic linear discriminant analysis or a global semi-tied covariance transform (also known as maximum likelihood linear transform [MLLT]). In some cases, an automatic speech recognition process may use discriminative training techniques, which may dispense with a purely statistical approach to HMM parameter estimation and instead optimize some classification-related measure of training data; examples may include maximum mutual information (MMI), minimum classification error (MCE), and minimum phone error (MPE).

With continued reference to FIG. 1, in some embodiments, an automatic speech recognition process may be said to decode speech (e.g., subject data 112 in audio format). Decoding of speech may occur when an automatic speech recognition system is presented with a new utterance and must compute a most likely sentence. In some cases, speech decoding may include a Viterbi algorithm. A Viterbi algorithm may include a dynamic programming algorithm for obtaining a maximum a posteriori probability estimate of a most likely sequence of hidden states (i.e., Viterbi path) that results in a sequence of observed events. Viterbi algorithms may be employed in context of Markov information sources and hidden Markov models. A Viterbi algorithm may be used to find a best path, for example using a dynamically created combination hidden Markov model, having both acoustic and language model information, using a statically created combination hidden Markov model (e.g., finite state transducer [FST] approach).

With continued reference to FIG. 1, in some embodiments, speech (e.g., subject data 112 in audio format) decoding may include considering a set of good candidates and not only a best candidate, when presented with a new utterance. In some cases, a better scoring function (i.e., re-scoring) may be used to rate each of a set of good candidates, allowing selection of a best candidate according to this refined score. In some cases, a set of candidates can be kept either as a list (i.e., N-best list approach) or as a subset of models (i.e., a lattice). In some cases, re-scoring may be performed by optimizing Bayes risk (or an approximation thereof). In some cases, re-scoring may include optimizing for sentence (including keywords) that minimizes an expectancy of a given loss function with regards to all possible transcriptions. For example, re-scoring may allow selection of a sentence that minimizes an average distance to other possible sentences weighted by their estimated probability. In some cases, an employed loss function may include Levenshtein distance, although different distance calculations may be performed, for instance for specific tasks. In some cases, a set of candidates may be pruned to maintain tractability.

With continued reference to FIG. 1, in some embodiments, an automatic speech recognition process may employ dynamic time warping (DTW)-based approaches. Dynamic time warping may include algorithms for measuring similarity between two sequences, which may vary in time or speed. For instance, similarities in walking patterns would be detected, even if in one video the person was walking slowly and if in another he or she were walking more quickly, or even if there were accelerations and deceleration during the course of one observation. DTW has been applied to video, audio, and graphics—indeed, any data that can be turned into a linear representation can be analyzed with DTW. In some cases, DTW may be used by an automatic speech recognition process to cope with different speaking (i.e., subject data 112 in audio format) speeds. In some cases, DTW may allow processor 104 to find an optimal match between two given sequences (e.g., time series) with certain restrictions. That is, in some cases, sequences can be "warped" non-linearly to match each other. In some cases, a DTW-based sequence alignment method may be used in context of hidden Markov models.

With continued reference to FIG. 1, in some embodiments, an automatic speech recognition process may include a neural network. Neural network may include any neural network, for example those disclosed with reference to FIGS. 4-6. In some cases, neural networks may be used for automatic speech recognition, including phoneme classification, phoneme classification through multi-objective evolutionary algorithms, isolated word recognition, audiovisual speech recognition, audiovisual speaker recognition and speaker adaptation. In some cases. neural networks employed in automatic speech recognition may make fewer explicit assumptions about feature statistical properties than HMMs and therefore may have several qualities making them attractive recognition models for speech recognition. When used to estimate the probabilities of a speech feature segment, neural networks may allow discriminative training in a natural and efficient manner. In some cases, neural networks may be used to effectively classify subject data 112 in audio format over short-time interval, for instance such as individual phonemes and isolated words. In some embodiments, a neural network may be employed by automatic speech recognition processes for pre-processing, feature transformation and/or dimensionality reduction, for example prior to HMM-based recognition. In some embodiments, long short-term memory (LSTM) and related recurrent neural networks (RNNs) and Time Delay Neural Networks (TDNN's) may be used for automatic speech recognition, for example over longer time intervals for continuous speech recognition.

With continued reference to FIG. 1, memory 108 contains instructions configuring processor 104 to retrieve peptide data 148 from a peptide database 152. For the purposes of this disclosure, "peptide data" is information related to a plurality of peptides. For the purposes of this disclosure, a "peptide" is a chain of amino acids linked together by peptide bonds. Amino acids are organic molecules that serve as the building blocks of proteins, and peptides can be thought of as small proteins or fragments of proteins. As a non-limiting example, peptide data 148 may include peptide sequences, structures, and known effects. As another non-limiting example, peptide data 148 may include data on peptide interactions, bioactivity tests, and therapeutic outcomes. The structure of peptides can be described in several levels. The primary structure refers to the linear sequence of amino acids in a peptide, held together by peptide bonds. The secondary structure involves local folding patterns within the peptide, such as alpha-helices and beta-sheets, which are stabilized by hydrogen bonds. The tertiary structure represents the overall three-dimensional shape of the peptide, determined by interactions between the side chains of the amino acids. Additionally, some peptides can interact to form more complex structures with other peptides or proteins, known as the quaternary structure, although this is more common in larger proteins. Peptides can be categorized based on the number of amino acids they contain. Dipeptides consist of two amino acids, tripeptides contain three amino acids, oligopeptides have a few amino acids typically fewer than 10-20, and polypeptides are longer chains of amino acids, containing 20-50 amino acids. Peptides may include a wide range of functions. As hormones, peptides like insulin and glucagon can regulate blood sugar levels. As neurotransmitters, peptides such as endorphins and substance P can play roles in transmitting signals in the nervous system. Some peptides can function as enzymes, catalyzing biochemical reactions, while antimicrobial peptides like defensins and cathelicidins protect against microbial infections. Peptides can also serve as signaling molecules, with cytokines mediating communication between cells, particularly in the immune system. Peptides can be used in developing medications for conditions like diabetes, cancer, and infectious diseases. They can also be employed in diagnostic tests to detect various diseases. In scientific research, peptides are used to study protein functions and interactions, understand disease mechanisms, and develop new therapeutic strategies.

With continued reference to FIG. 1, as used in this disclosure, "peptide database" is a data structure configured to store data associated with a plurality of peptides. In some embodiments, peptide database 152 may include published studies and proprietary research. In some embodiments, peptide database 152 may include public databases like Protein Data Bank, PubChem, and the like. In some embodiments, processor 104 may receive peptide data 148 from a remote device 132. As a non-limiting example, third party may manually input peptide data 148 into processor 104 using remote device 132. In some embodiments, peptide database 152 may be consistent with any database disclosed in this disclosure.

With continued reference to FIG. 1, in some embodiments, peptide data 148 may be derived from a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, processor 104 may generate web crawler to scrape peptide data 148 from websites such as research website, and the like. The web crawler may be seeded and/or trained with a reputable website to begin the search. Web crawler may be generated by processor 104. In some embodiments, web crawler may be trained with information received from third party through a user interface. In some embodiments, web crawler may be configured to generate a web query. A web query may include search criteria received from third party. For example, third party may submit a plurality of websites for web crawler to search to peptide data 148. Additionally, web crawler function may be configured to search for and/or detect one or more data patterns. A "data pattern" as used in this disclosure is any repeating forms of information. In some embodiments, web crawler may be configured to determine the relevancy of a data pattern. Relevancy may be determined by a relevancy score. A relevancy score may be automatically generated by processor 104, received from a machine-learning model, and/or received from user. In some embodiments, a relevancy score may include a range of numerical values that may correspond to a relevancy strength of data received from a web crawler function. As a non-limiting example, a web crawler function may search the Internet for peptide data 148.

With continued reference to FIG. 1, memory 108 contains instructions configuring processor 104 to convert peptide data 148 into a machine-readable input 156. For the purposes of this disclosure, a "machine-readable input" is data formatted in a way that can be processed by computer systems or algorithms. Processor 104 may convert peptide data 148 into a format suitable for stack machine-learning model 160, such as numerical encoding of amino acid sequences or structural features like hydrophobicity, charge, size, and the like. Peptide data 148 may be structured in such a way that it can be interpreted, analyzed, and used by processor 104 without requiring manual intervention or translation. In some embodiments, machine-readable input 156 may include numerical data, encoded text, structured datasets, and other formats that processor 104 can process directly. As a non-limiting example, peptide sequences may be converted into numerical representations using one-hot encoding or integer encoding. For example, and without limitation, for the peptide sequence "GAVFL," it may be converted to "G: [1, 0, 0, . . . , 0], A: [0, 1, 0, . . . , 0], V: [0, 0, 1, . . . , 0], F: [0, 0, 0, 1, . . . , 0], L: [0, 0, 0, 0, 1, . . . , 0]" or "G: 1, A: 2, V: 3, F: 4, L: 5." As another non-limiting example, the structure of peptides may be converted into numerical formats that capture spatial and geometric information using 3D coordinates and distance matrices. For example, and without limitation, a peptide's 3D coordinates might be represented as "(x1, y1, z1), (x2, y2, z2), . . . , (xn, yn, zn)." As another non-limiting example, physicochemical properties such as molecular weight, isoelectric point, hydrophobicity, and solubility may be translated into numerical values that can be input into stack machine-learning model 160. For example, and without limitation, a vector for a peptide may look like "[molecular weight: 500, isoelectric point: 7.4, hydrophobicity: 0.8, binding affinity: 0.95]." In some embodiments, machine-readable input 156 may be stored in peptide database 152. In some embodiments, processor 104 may retrieve machine-readable input 156 from peptide database 152. In some embodiments, third party may manually input machine-readable input 156. Converting data into a machine-readable format involves various methods, each suited for different types of data and analytical needs. In some embodiments, processor 104 may convert peptide data 148 to machine-readable input 156 using label encoding, embeddings, Bag-of-Words, TF-IDF, one-hot encoding with position, PSSMs, PCA, autoencoders, Fourier transform, graph-based methods, sparse coding, and/or kernel methods.

With continued reference to FIG. 1, memory 108 contains instructions configuring processor 104 to generate a peptide stack datum 116 as a function of subject data 112 and machine-readable input 156. For the purposes of this disclosure, a "peptide stack datum" is a data element related to a combination of at least two peptides of a plurality of peptides that are compatible to subject data. As a non-limiting example, peptide stack datum 116 may include Growth Hormone Releasing Peptides (GHRPs) such as GHRP-2 or GHRP-6, which stimulate the release of growth hormone from the pituitary gland, combined with CJC-1295, a Growth Hormone Releasing Hormone (GHRH) analog that extends the half-life of the growth hormone released. As another non-limiting example, peptide stack datum 116 may include Thymosin Beta-4 (TB-500) for its tissue repair and anti-inflammatory properties, alongside Epitalon, which can promote longevity by regulating the pineal gland and increasing telomerase activity. In some embodiments, peptide stack datum 116 may be stored in peptide database 152. In some embodiments, processor 104 may retrieve peptide stack datum 116 from peptide database 152. In some embodiments, third party may manually input peptide stack datum 116.

With continued reference to FIG. 1, in some embodiments, generating peptide stack datum 116 may include determining at least two peptides from a plurality of peptides from peptide data 148 and determining a ratio datum 120 and/or dosage datum of the at least two peptides. In a non-limiting example, each peptide of a plurality of peptides (e.g., peptide data 148) may include intended function; for instance, one peptide might promote muscle growth while another reduces inflammation. In some embodiments, processor 104 may determine at least two peptides as a function of target datum 164 as described below. In a non-limiting example, processor 104 may determine at least two peptides that can achieve desired outcomes or therapeutic goals that a third party or user aims to achieve for the user's health. For the purposes of this disclosure, a "dosage datum" is a data element related to the precise amount of peptide. As a non-limiting example, dosage datum may include the amount of peptide in units such as milligrams (mg), micrograms (mcg), or milliliters (mL). For the purposes of this disclosure, a "ratio datum" is a data element related to the proportions or relative amounts of peptides. For example, and without limitation, for peptide A, dosage datum may include 10 mg per day, for peptide B, dosage datum may include 5 mg per day, and processor 104 may determine ratio datum 120 to be a 2:1 ratio of peptide A to peptide B (i.e., 10 mg of peptide A to 5 mg of peptide B). In some embodiments, ratio datum 120 and/or dosage datum may be stored in peptide database 152. In some embodiments, processor 104 may retrieve ratio datum 120 and/or dosage datum from peptide database 152. In some embodiments, third party may manually input ratio datum 120 and/or dosage datum. In some embodiments, processor 104 may determine ratio datum 120 and/or dosage datum through the use of machine-learning model. In a non-limiting example, processor 104 may determine ratio datum 120 and/or dosage datum using a ratio machine-learning model that may be trained with ratio training data, wherein ratio training data may include correlation of exemplary peptides and ratio datums and/or dosage datums. The ratio machine-learning model may be consistent with any machine-learning models disclosed in this disclosure.

With continued reference to FIG. 1, in some embodiments, generating peptide stack datum 116 may include identifying a target datum 164 from peptide request datum 128 and generating peptide stack datum 116 as a function of the target datum 164. In some embodiments, processor 104 may determine at least two peptides from a plurality of peptides from peptide data 148 and generate peptide stack datum 116 as a function of target datum 164. For the purposes of this disclosure, a "target datum" is a data element related to a goal or objective for the effect of peptide stacks. In a non-limiting example, target datum 164 may include desired outcomes or therapeutic goals that a third party or user aims to achieve for the user by using peptide stack based on the user's individual health and requests. In a non-limiting example, peptide stack datum 116 may include a combination of peptides to enhance certain biological effects that a user or third party wants (e.g., target datum 164). As a non-limiting example, target datum 164 may include improving muscle growth, enhancing cognitive function, reducing inflammation, managing blood glucose levels, and the like. As another non-limiting example, target datum 164 may include fat loss, tissue repair, and hormone production. In some embodiments, target datum 164 may be stored in peptide database 152. In some embodiments, processor 104 may retrieve target datum 164 from peptide database 152. In some embodiments, third party may manually input target datum 164.

With continued reference to FIG. 1, in some embodiments, processor 104 may identify target datum 164 from peptide request datum 128 using a language processing module 168 168. In some embodiments, processor 104 may use a language processing module 168 to find a keyword (e.g., target datum 164) from subject data 112 (e.g., peptide request datum 128) in textual format. The language processing module 168 may be configured to extract one or more words related to target datum 164 from peptide request datum 128. One or more words may include, without limitation, strings of one or more characters, including without limitation any sequence or sequences of letters, numbers, punctuation, diacritic marks, medical terms, chemical symbols and formulas, spaces, whitespace, and other symbols, including any symbols usable as target datum 164. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams," where all sequences of n consecutive characters are considered. Any or all possible sequences of tokens or words may be stored as "chains," for example for use as a Markov chain or Hidden Markov Model.

With continued reference to FIG. 1, language processing module 168 may operate to produce a language processing model. Language processing model may include a program automatically generated by processor 104 and/or language processing module 168 to produce associations between one or more words extracted from at least a document and detect associations, including without limitation mathematical associations, between such words. Associations between language elements, where language elements include for purposes herein extracted words, relationships of such categories to other such term may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of semantic meaning. As a further example, statistical correlations and/or mathematical associations may include probabilistic formulas or relationships indicating a positive and/or negative association between at least an extracted word and/or a given semantic meaning; positive or negative indication may include an indication that a given document is or is not indicating a category semantic meaning. Whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at computing device, or the like.

With continued reference to FIG. 1, language processing module 168 may generate the language processing model by any suitable method, including without limitation a natural language processing classification algorithm; language processing model may include a natural language process classification model that enumerates and/or derives statistical relationships between input terms and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs, as used herein, are statistical models with inference algorithms that that may be applied to the models. In such models, a hidden state to be estimated may include an association between an extracted words, phrases, and/or other semantic units. There may be a finite number of categories to which an extracted word may pertain; an HMM inference algorithm, such as the forward-backward algorithm or the Viterbi algorithm, may be used to estimate the most likely discrete state given a word or sequence of words. Language processing module 168 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

With continued reference to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

With continued reference to FIG. 1, language processing module 168 may use a corpus of documents to generate associations between language elements in a language processing module 168 may then use such associations to analyze words extracted from one or more documents and determine that the one or more documents indicate significance of a category. In an embodiment, language module and/or processor 104 may perform this analysis using a selected set of significant documents, such as documents identified by one or more experts as representing good information; experts may identify or enter such documents via graphical user interface or may communicate identities of significant documents according to any other suitable method of electronic communication, or by providing such identity to other persons who may enter such identifications into processor 104. Documents may be entered into a computing device by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, processor 104 may automatically obtain the document using such an identifier, for instance by submitting a request to a database or compendium of documents such as JSTOR as provided by Ithaka Harbors, Inc. of New York.

With continued reference to FIG. 1, in some embodiments, processor 104 may identify target datum 164 as a function of user condition data 124. In a non-limiting example, processor 104 may identify any body function or health that can be or should be improved (e.g., target datum 164) based on a user's health condition or medical test results. In some embodiments, processor 104 may identify target datum 164 using a target machine-learning model. In some embodiments, processor 104 may be configured to generate target training data. In a non-limiting example, target training data may include correlations between exemplary user condition data correlated to exemplary peptide stack datums. In some embodiments, target training data may be stored in subject database. In some embodiments, target training data may be received from one or more users, subject database, external computing devices, and/or previous iterations of processing. As a non-limiting example, target training data may include instructions from a user, who may be an expert user, a past user in embodiments disclosed herein, or the like, which may be stored in memory and/or stored in subject database, where the instructions may include labeling of training examples. In some embodiments, target training data may be updated iteratively on a feedback loop. As a non-limiting example, processor 104 may update target training data iteratively through a feedback loop as a function of output of LLM 136, subject data 112, user condition data 124, peptide data 148, machine-readable input 156, and the like. In some embodiments, processor 104 may be configured to generate target machine-learning model. In a non-limiting example, generating target machine-learning model may include training, retraining, or fine-tuning target machine-learning model using target training data or updated target training data. In some embodiments, processor 104 may be configured to determine target datum 164 using target machine-learning model (i.e. trained or updated target machine-learning model). In some embodiments, user may be classified to a user cohort using a cohort classifier. Cohort classifier may be consistent with any classifier discussed in this disclosure. Cohort classifier may be trained on cohort training data, wherein the cohort training data may include subject data correlated to user cohorts. In some embodiments, a user or subject data 112 (e.g., user condition data 124) may be classified to a user cohort and processor 104 may determine peptide stack datum 116 based on the user cohort using a machine-learning module as described in detail with respect to FIG. 4 and the resulting output may be used to update target training data. In some embodiments, generating training data and training machine-learning models may be simultaneous.

With continued reference to FIG. 1, determining peptide stack datum 116 includes generating stack training data 172, wherein the stack training data 172 includes exemplary subject data and exemplary machine-readable inputs correlated to exemplary peptide stack datums, training a stack machine-learning model 160 trained with stack training data 172 and generating peptide stack datum 116 using the trained stack machine-learning model 160. In some embodiments, stack training data 172 may be stored in peptide database 152. In some embodiments, stack training data 172 may be received from one or more users, peptide database 152, external computing devices, and/or previous iterations of processing. As a non-limiting example, stack training data 172 may include instructions from a user, who may be an expert user, a past user in embodiments disclosed herein, or the like, which may be stored in memory and/or stored in peptide database 152, where the instructions may include labeling of training examples. In some embodiments, stack training data 172 may be updated iteratively on a feedback loop. As a non-limiting example, processor 104 may update stack training data 172 iteratively through a feedback loop as a function of output of ratio machine-learning model, target machine-learning model, LLM 136, and the like, subject data 112, user condition data 124, peptide request datum 128, peptide data 148, and the like. In a non-limiting example, generating stack machine-learning model 160 may include training, retraining, or fine-tuning stack machine-learning model 160 using stack training data 172 or updated stack training data 172. In some embodiments, processor 104 may be configured to determine peptide stack datum 116 using stack machine-learning model 160 (i.e. trained or updated stack machine-learning model 160). In some embodiments, stack machine-learning model 160 may include machine-learning algorithms for sequence prediction (e.g., stacking peptides with different bases, such as combining growth hormone-releasing peptides with mitochondrial peptides) and optimization. In some embodiments, stack machine-learning model 160 may include deep learning models like recurrent neural networks (RNNs) or convolutional neural networks (CNNs). In some embodiments, stack machine-learning model 160 may use cross-validation techniques to test the model's predictive accuracy. In peptide sequence generation, stack machine-learning model 160 may implement optimization algorithms, possibly reinforcement learning to find the best combinations of peptides that maximize the desired effect while minimizing potential side effects. In some embodiments, user may be classified to a user cohort using a cohort classifier. Cohort classifier may be consistent with any classifier discussed in this disclosure. Cohort classifier may be trained on cohort training data, wherein the cohort training data may include subject data 112 correlated to user cohorts. In some embodiments, a user may be classified to a user cohort and processor 104 may determine peptide stack datum 116 based on the user cohort using a machine-learning module as described in detail with respect to FIG. 3 and the resulting output may be used to update stack training data 172. In some embodiments, generating training data and training machine-learning models may be simultaneous.

With continued reference to FIG. 1, in some embodiments, generating peptide stack datum 116 may include generating a simulation model 176 and simulating peptide stack datum 116 using the simulation model 176. For the purposes of this disclosure, a "simulation model" is a computational model that can simulate the interactions and effects of peptides. In a non-limiting example, simulation of peptide stack datum 116 using simulation model 176 may include in silico testing. For the purposes of this disclosure, an "in silico testing" refers the use of computer models and simulations to predict the behavior of drugs, chemicals, or biological processes in real-world scenarios. In silico testing can identify potential issues, optimize peptide combinations, and refine dosage regimens. In some embodiments, processor 104 may determine appropriate machine-learning algorithms and computational methods, such as molecular dynamics simulations, quantitative structure-activity relationship (QSAR) models, or neural networks for simulation model 176 and may simulate peptide stack datum 116 using simulation model 176. In some embodiments, processor 104 may be configured to run simulations to predict how the peptides of peptide stack datum 116 will interact with each other and with a user's body. In a non-limiting example, simulating the interaction of IGF-1 LR3, TB-500, and BPC-157 of peptide stack datum 116 may reveal how these peptides collectively enhance muscle growth and recovery, and whether their combined use might lead to unforeseen interactions or enhanced effects. In some embodiments, generating peptide stack datum 116 may include updating stack training data 172 as a function of the simulation, retraining stack machine-learning model 160 using the updated stack training data 172 and generating peptide stack datum 116 using the retrained stack machine-learning model 160. In a non-limiting example, if the simulation predicts that peptides of peptide stack datum 116 are not compatible or does not achieve target datum 164, processor 104 may update stack training data 172 to include information that the peptides are not compatible or does not achieve target datum 164, retrain stack machine-learning model 160 and regenerate peptide stack datum 116 using the retrained stack machine-learning model 160. In some embodiments, processor 104 may determine ratio datum 120 as a function of simulation. As a non-limiting example, simulation model 176 may predict the interactions and effects of different peptide ratios and this may identify the most effective combinations and concentrations of at least two peptides of peptide stack datum 116.

With continued reference to FIG. 1, memory 108 contains instructions configuring processor 104 to generate a user interface 180 displaying peptide stack datum 116 on a remote device 132. In some embodiments, processor 104 may be further configured to generate a user interface 180 displaying subject data 112, peptide data 148, machine-readable input 156, peptide stack datum 116, user condition data 124, peptide request datum 128, ratio datum 120, target datum 164, user prompt 144, and the like. For the purposes of this disclosure, a "user interface" is a means by which a user or third party and a computer system interact; for example through the use of input devices and software. A user interface 180 may include a graphical user interface (GUI), command line interface (CLI), menu-driven user interface, touch user interface, voice user interface (VUI), form-based user interface, any combination thereof and the like. In some embodiments, user interface 180 may operate on and/or be communicatively connected to a decentralized platform, metaverse, and/or a decentralized exchange platform associated with user or third party. For example, a user or third party may interact with user interface in virtual reality. In some embodiments, a user or third party may interact with the user interface 180 using a computing device distinct from and communicatively connected to at least a processor 104. For example, a smart phone, smart, tablet, or laptop operated by a user or third party. In an embodiment, user interface 180 may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. In some embodiments, user interface 180 may include search functions that allows a user or third party to look up optimal peptide stacks (e.g., peptide stack datum 116) for specific conditions or desired outcomes (e.g., target datum 164). In some embodiments, user interface 180 may include interactive tools to visualize data trends and correlations between different health parameters and treatment responses. In some embodiments, user interface 180 may include generate secure access protocols to ensure subject data confidentiality and compliance with healthcare regulations.

With continued reference to FIG. 1, in some embodiments, processor 104 may categorize subject data 112 and peptide stack datum 116 as a function of target datum 164, generate a categorized database 184 as a function of subject data 112 and peptide stack datum 116 categorized to the categorized subject data 112 and the peptide stack datum 116 and generate user interface 180 that enables a third party to access and interact with data within the categorized database 184. As used in this disclosure, "categorized database" is a data structure configured to store and organize data associated with subject data and peptide stack datum. In a non-limiting example, processor 104 may categorize subject data 112 (e.g., user condition data 124) and the corresponding peptide stack datum 116 based on target datum 164. For example, and without limitation, user condition data 124, such as protein synthesis levels, muscle mass measurements, and the like and peptide stack datum 116 (e.g., IGF-1 LR3, TB-500) may be categorized under "muscle growth" target datum 164. Once subject data 112 and peptide stack datum 116 are categorized, processor 104 may generate a categorized database 184 that organizes this information for retrieval and analysis. The categorized database 184 may index the categorized subject data 112 and peptide stack datum 116, allowing for quick access based on specific targets (e.g., target datum 164). In some embodiments, categorized database 184 may include a search index. A "search index" as used in this disclosure is a data structure that is configured to compare and/or match data. A search index may be used to link two or more data elements of categorized database 184. A search index may enable faster lookup times by linking similar data elements, such as subject data 112, user condition data 124, target datum 164, and/or peptide stack datum 116. In some embodiments, processor 104 may generate an index classifier. In an embodiment, an index classifier may include a classifier. A "classifier," as used in this disclosure is a machine-learning model, such as a mathematical model, neural net, or program generated by a machine-learning algorithm known as a "classification algorithm," as described in further detail below, that sorts inputs into categories or bins of data, outputting the categories or bins of data and/or labels associated therewith. An index classifier may include a classifier configured to input subject data 112, user condition data 124, target datum 164, and/or peptide stack datum 116 and output indices. In some embodiments, processor 104 may generate a database indexing values from subject data 112 (e.g., glucose levels, inflammatory markers, microbiome composition, and the like) correlated to peptide stacks (e.g., peptide stack datum 116) categorized by desired health outcomes (e.g., target datum 164) such as muscle growth, fat loss, anti-aging, or improved immune function.

With continued reference to FIG. 1, in some embodiments, processor 104 may identify an outlier datum 188 as a function of subject data 112, generate an outlier control datum 192 as a function of the outlier datum 188 and generate user interface 180 displaying the outlier control datum 192 on a remote device 132. For the purposes of this disclosure, an "outlier datum" is a data element related to values or patterns that deviate from the norm. As a non-limiting example, outlier datum 188 may include rare or less common medical disorders, unique genetic traits, and other atypical health conditions. In some embodiments, processor 104 may determine outlier datum 188 as a function of user condition data 124. In some embodiments, processor 104 may determine peptide stack datum 116 as a function of outlier datum 188. In some embodiments, stack training data 172 may include exemplary outlier datum correlated to exemplary peptide stack datums and stack machine-learning model 160 trained with the stack training data 172 may generate peptide stack datum 116 as a function of outlier datum 188, where peptide stack datum 116 may include at least two peptides that can overcome or treat outlier datum 188. In some embodiments, third party may manually input outlier datum 188. In some embodiments, processor 104 may determine outlier datum 188 using an outlier machine-learning model. In some embodiments, processor 104 may be configured to generate outlier training data. In a non-limiting example, outlier training data may include correlations between exemplary user condition data correlated to exemplary outlier datums. In some embodiments, outlier training data may be stored in subject database. In some embodiments, outlier training data may be received from one or more users, subject database, external computing devices, and/or previous iterations of processing. As a non-limiting example, outlier training data may include instructions from a user, who may be an expert user, a past user in embodiments disclosed herein, or the like, which may be stored in memory and/or stored in subject database, where the instructions may include labeling of training examples. In some embodiments, outlier training data may be updated iteratively on a feedback loop. As a non-limiting example, processor 104 may update outlier training data iteratively through a feedback loop as a function of output of LLM 136, stack machine-learning model 160, and the like, subject data 112, user condition data 124, peptide data 148, machine-readable input 156, peptide stack datum 116, and the like. In some embodiments, processor 104 may be configured to generate outlier machine-learning model. In a non-limiting example, generating outlier machine-learning model may include training, retraining, or fine-tuning outlier machine-learning model using outlier training data or updated outlier training data. In some embodiments, processor 104 may be configured to determine target datum 164 using outlier machine-learning model (i.e. trained or updated outlier machine-learning model). In some embodiments, user may be classified to a user cohort using a cohort classifier. Cohort classifier may be consistent with any classifier discussed in this disclosure. Cohort classifier may be trained on cohort training data, wherein the cohort training data may include subject data correlated to user cohorts. In some embodiments, a user or subject data 112 (e.g., user condition data 124) may be classified to a user cohort and processor 104 may determine peptide stack datum 116 based on the user cohort using a machine-learning module as described in detail with respect to FIG. 3 and the resulting output may be used to update outlier training data. In some embodiments, generating training data and training machine-learning models may be simultaneous.

With continued reference to FIG. 1, for the purposes of this disclosure, an "outlier control datum" is a data element related to a method for controlling the outlier datum. As a non-limiting example, outlier control datum 192 may include appointment scheduling with a health professional, notifying a user or third party related to outlier datum 188, and the like. In some embodiments, processor 104 may evaluate the nature of outlier datum 188 to recommend the appropriate type of health professional, such as a specialist in cardiology, endocrinology, or genetics. For example, and without limitation, increase in inflammatory markers (e.g., outlier datum 188) may require consultation with a specialist in immunology (e.g., outlier control datum 192). In a non-limiting example, processor 104 may generate outlier control datum 192 that includes a notification: "Your recent blood test indicates an increase in inflammatory markers. We recommend scheduling an appointment with an immunologist for further evaluation. Please confirm your availability."

Figure 2:
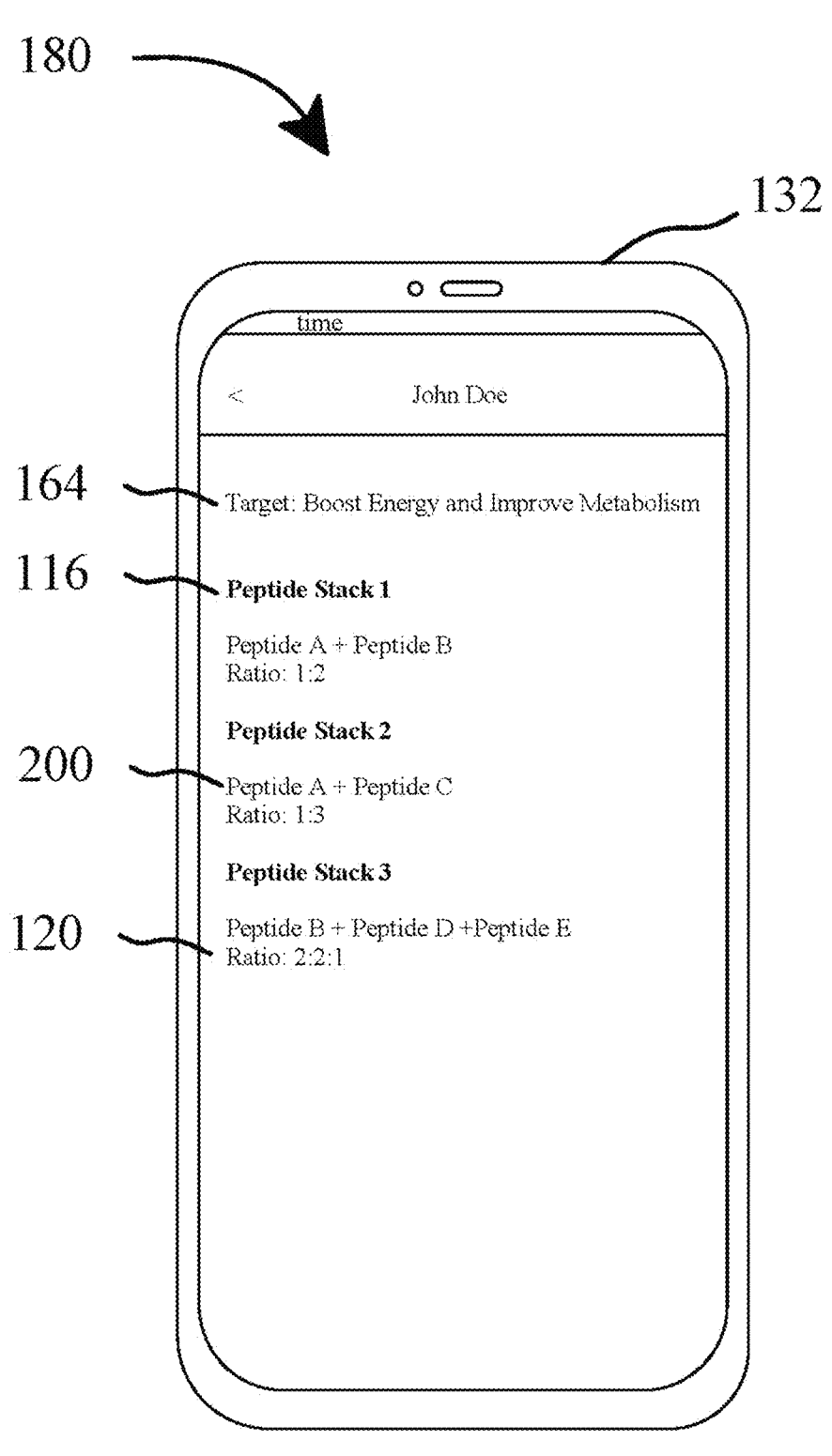
FIG. 2 illustrates a configuration of an exemplary user interface on a remote device.

Referring now to FIG. 2, a configuration of an exemplary user interface 180 on a remote device 132 is illustrated. In some embodiments, processor 104 may generate user interface 180 displaying subject data 112, user condition data 124, peptide request datum 128, user prompt 144, peptide data 148, peptide stack datum 116, ratio datum 120, outlier datum 188, outlier control datum 192, target datum 164, and the like on remote device 132. As a non-limiting example, remote device 132 may include a laptop, desktop, tablet, mobile phone, smart phone, smart watch, kiosk, screen, smart headset, or things of the like. In a non-limiting example, user interface 180 may display target datum 164 as 'Boost Energy and Improve Metabolism." In a non-limiting example, user interface 180 may display a plurality of peptide stack datums 116. For example, and without limitation, processor 104 may determine a plurality of peptide stack datums 116 that matches with target datum 164 and may generate user interface 180 displaying the plurality of peptide stack datums 116. In a non-limiting example, user interface 180 may display any metadata related to a plurality of peptide stack datums 116, such as names 200 of peptides in peptide stacks, ratio datum 120, dosage datum, and the like.

Figure 3:
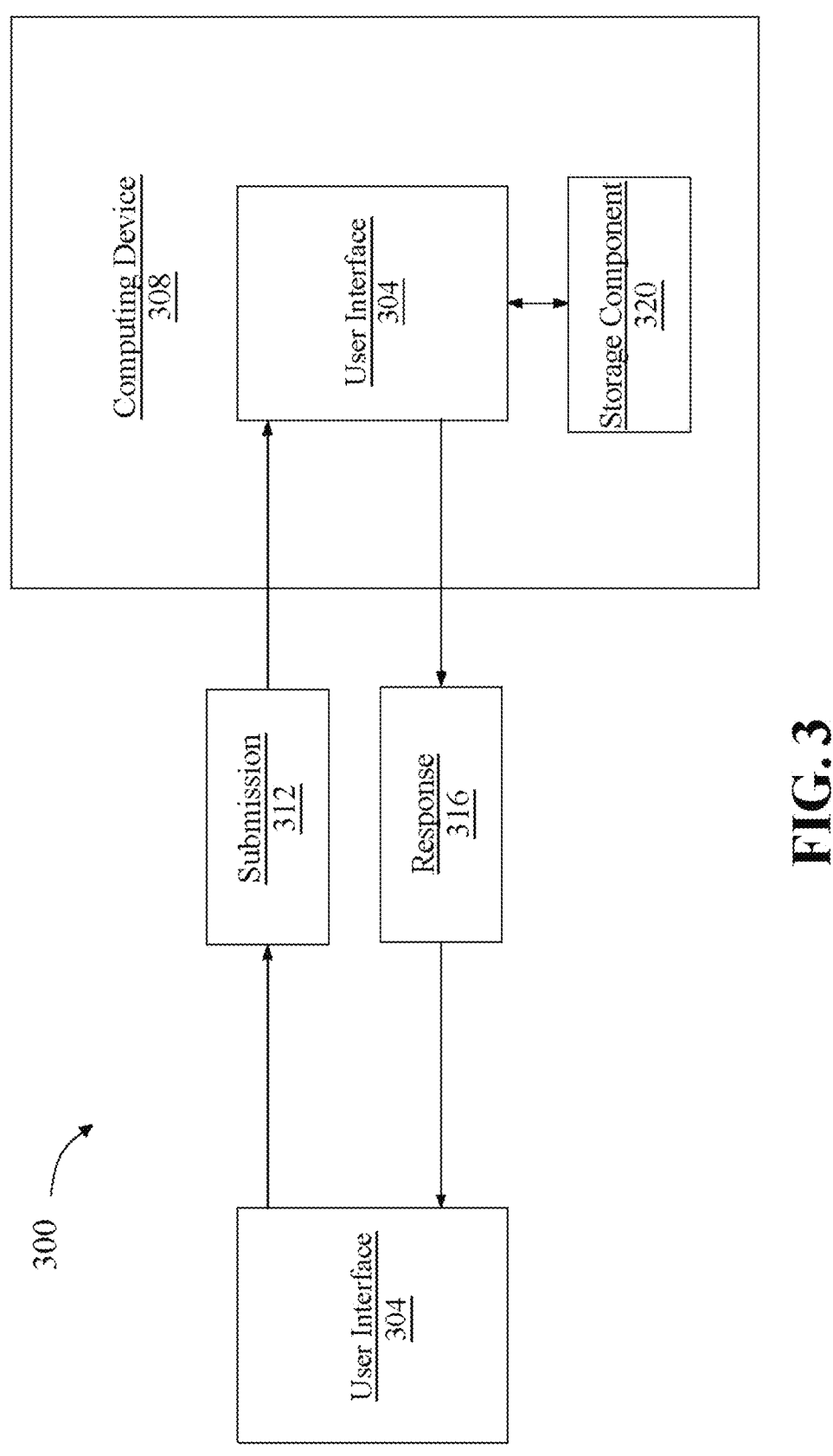
FIG. 3 illustrates a block diagram of an exemplary chatbot system.

Referring to FIG. 3, a chatbot system 300 is schematically illustrated. According to some embodiments, a user interface 304 may be communicative with a computing device 308 that is configured to operate a chatbot. In some cases, user interface 304 may be local to computing device 308. Alternatively or additionally, in some cases, user interface 304 may remote to computing device 308 and communicative with the computing device 308, by way of one or more networks, such as without limitation the internet. Alternatively or additionally, user interface 304 may communicate with computing device 308 using telephonic devices and networks, such as without limitation fax machines, short message service (SMS), or multimedia message service (MMS). Commonly, user interface 304 communicates with computing device 308 using text-based communication, for example without limitation using a character encoding protocol, such as American Standard for Information Interchange (ASCII). Typically, a user interface 304 conversationally interfaces a chatbot, by way of at least a submission 312, from the computing device 308 to the chatbot, and a response 316, from the chatbot to the user interface 304. In many cases, one or both of submission 312 and response 316 are text-based communication. Alternatively or additionally, in some cases, one or both of submission 312 and response 316 are audio-based communication.

Continuing in reference to FIG. 3, a submission 312 once received by computing device 308 operating a chatbot, may be processed by a processor. In some embodiments, processor processes a submission 312 using one or more of keyword recognition, pattern matching, and natural language processing. In some embodiments, processor employs real-time learning with evolutionary algorithms. In some cases, processor may retrieve a pre-prepared response from at least a storage component 320, based upon submission 312. Alternatively or additionally, in some embodiments, processor communicates a response 316 without first receiving a submission 312, thereby initiating conversation. In some cases, processor communicates an inquiry to user interface 304; and the processor is configured to process an answer to the inquiry in a following submission 312 from the user interface 304. In some cases, an answer to an inquiry present within a submission 312 from a user interface 304 may be used by computing device 308 as an input to another function.

With continued reference to FIG. 3, a chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "chatbot input" is any response that a user or third party inputs into a chatbot as a response to a prompt or question.

With continuing reference to FIG. 3, computing device 308 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 308 may generate two or more decision trees, which may overlap; for instance, a root node of one tree may connect to and/or receive output from one or more terminal nodes of another tree, intermediate nodes of one tree may be shared with another tree, or the like.

With continued reference to FIG. 3, computing device 308 may build decision tree by following relational identification; for example, relational indication may specify that a first rule module receives an input from at least a second rule module and generates an output to at least a third rule module, and so forth, which may indicate to computing device 308 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 308 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure.

Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

With continued reference to FIG. 3, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Figure 4:
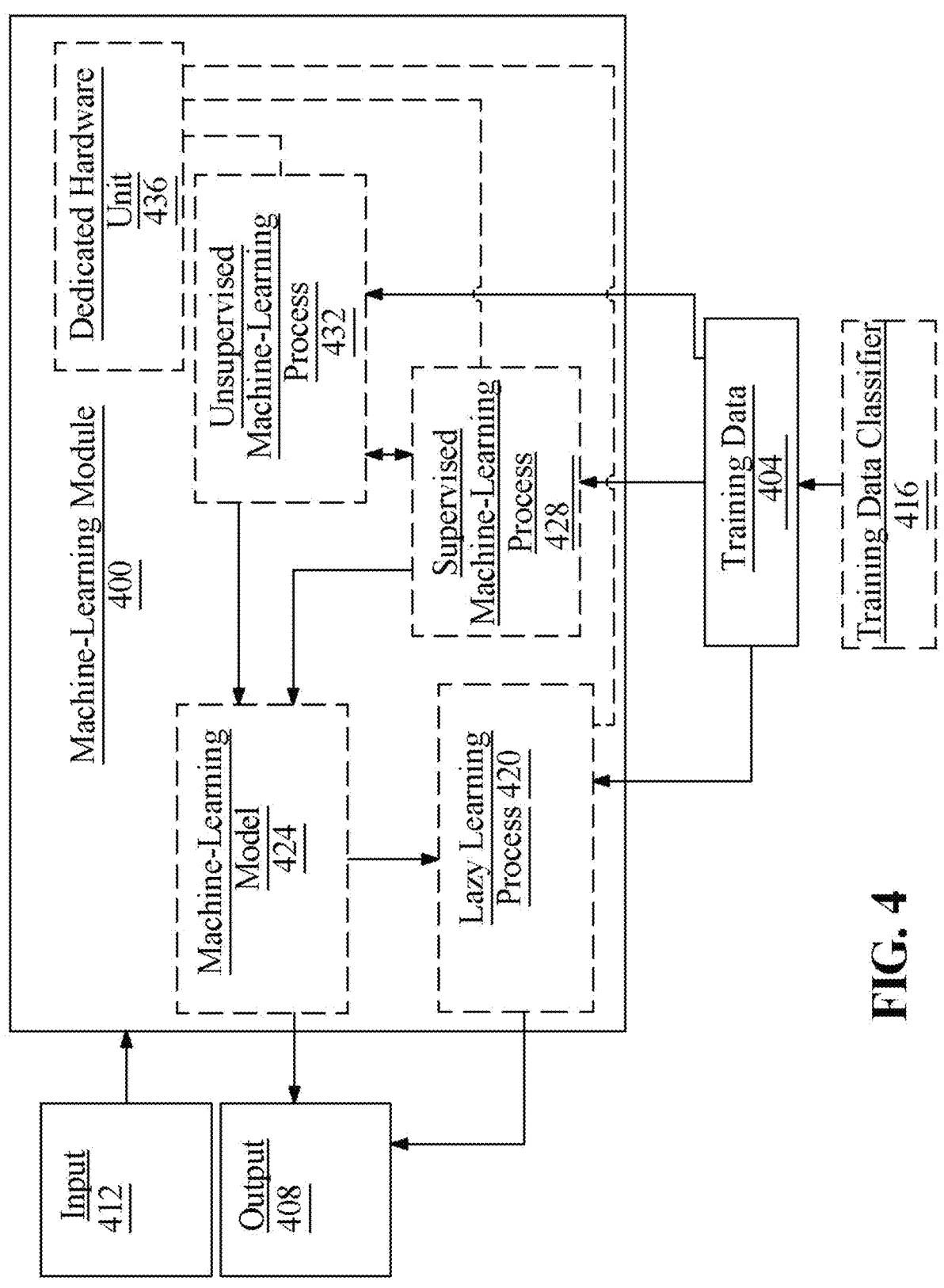
FIG. 4 illustrates a block diagram of an exemplary machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine-learning processes. A "machine-learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine-learning software program where the commands to be executed are determined in advance by a user and written in a programming language.

With continued reference to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and with continued reference to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example, input data may include subject data 112, user condition data 124, peptide request datum 128, peptide data 148, machine-readable input 156, target datum 164, outlier datum 188, and the like. As a non-limiting illustrative example, output data may include subject data 112, user condition data 124, peptide request datum 128, peptide data 148, machine-readable input 156, target datum 164, outlier datum 188, peptide stack datum 116, ratio datum 120, outlier control datum 192, and the like.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to user cohorts. For example, and without limitation, training data classifier 416 may classify elements of training data to user cohorts related to users' age, gender, weight, lifestyle habits, medical history, treatment experience, and the like.

With continued reference to FIG. 4, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute $l$ as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, subject data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

With continued reference to FIG. 4, computer, processor, and/or module may be configured to preprocess training data. "Preprocessing" training data, as used in this disclosure, is transforming training data from raw form to a format that can be used for training a machine-learning model. Preprocessing may include sanitizing, feature selection, feature scaling, data augmentation and the like.

With continued reference to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

With continued reference to FIG. 4, computing device, processor, and/or module may be configured to precondition one or more training examples. For instance, and without limitation, where a machine-learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine-learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine-learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}:X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

With continued reference to FIG. 4, machine-learning module 400 may be configured to perform a lazy-learning process 420 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

With continued reference to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include subject data 112, user condition data 124, peptide request datum 128, peptide data 148, machine-readable input 156, target datum 164, outlier datum 188, and the like as described above as inputs, subject data 112, user condition data 124, peptide request datum 128, peptide data 148, machine-readable input 156, target datum 164, outlier datum 188, peptide stack datum 116, ratio datum 120, outlier control datum 192, and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

With continued reference to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine-learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

With continued reference to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

With continued reference to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

With continued reference to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

With continued reference to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
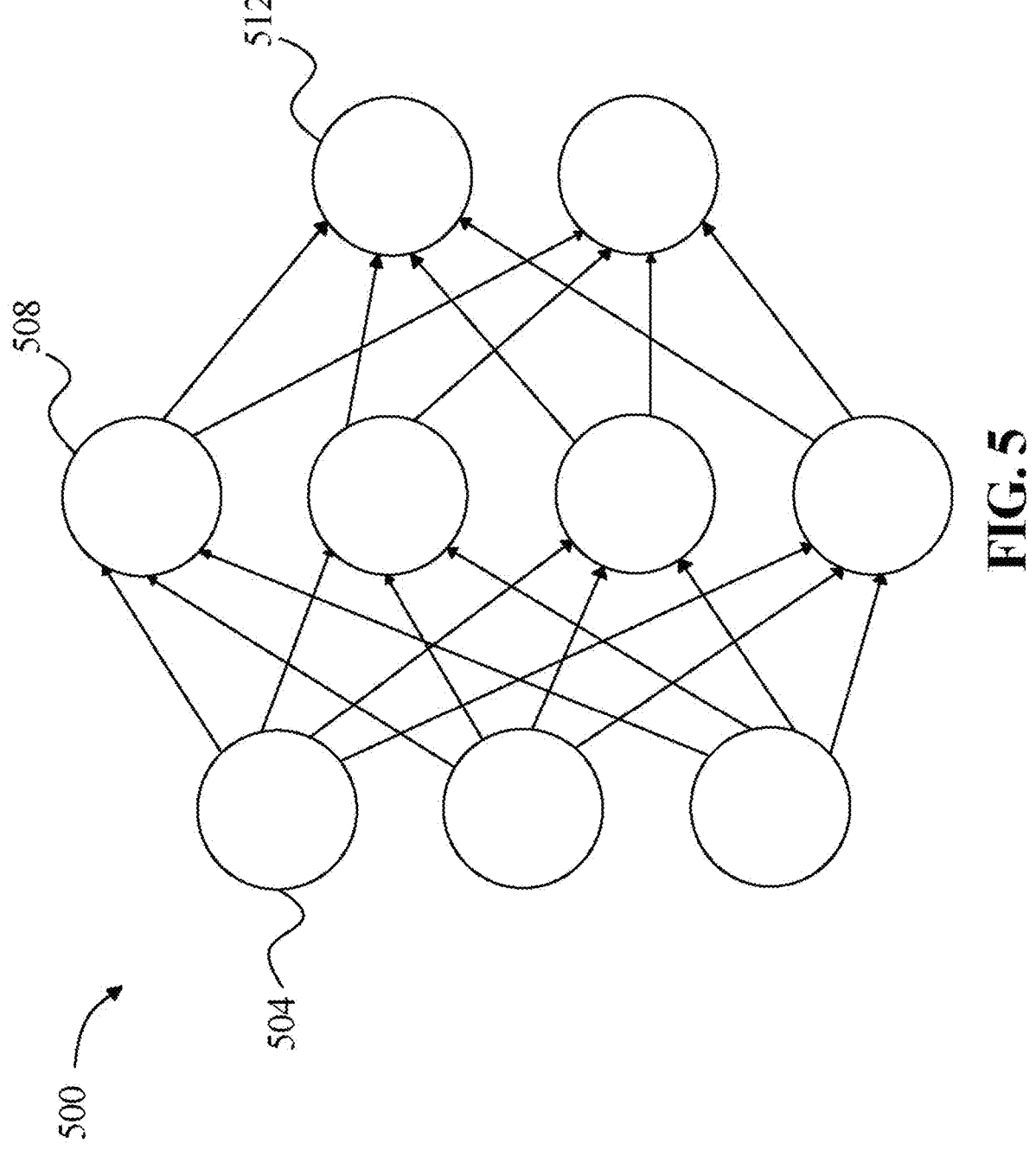
FIG. 5 illustrates a diagram of an exemplary neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
FIG. 6 illustrates a block diagram of an exemplary node in a neural network.

Referring now to FIG. 6 an exemplary embodiment of a node 600 of a neural network is illustrated. A node may include, without limitation, a plurality of inputs $x_1$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x) = \tanh^2(x)$, a rectified linear unit function such as $f(x) = \max(0, x)$, a "leaky" and/or "parametric" rectified linear unit function such as $f(x) = \max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of a (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x) = x*\text{sigmoid}(x)$, a Gaussian error linear unit function such as $f(x) = a(1 + \tanh(\sqrt{2/\pi}(x + bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Referring now to FIG. 7, an exemplary categorized database 184 is illustrated. In a non-limiting example, processor 104 may categorize subject data 112 (e.g., user condition data 124) and the corresponding peptide stack datum 116 based on target datum 164. For example, and without limitation, user condition data 124, such as protein synthesis levels, muscle mass measurements, and the like and peptide stack datum 116 (e.g., IGF-1 LR3, TB-500) may be categorized under "muscle growth and anti-aging" target datum 164. Once subject data 112 and peptide stack datum 116 are categorized, processor 104 may generate a categorized database 184 that organizes this information for retrieval and analysis. The categorized database 184 may index the categorized subject data 112 and peptide stack datum 116, allowing for quick access based on specific targets (e.g., target datum 164).

Figure 8:
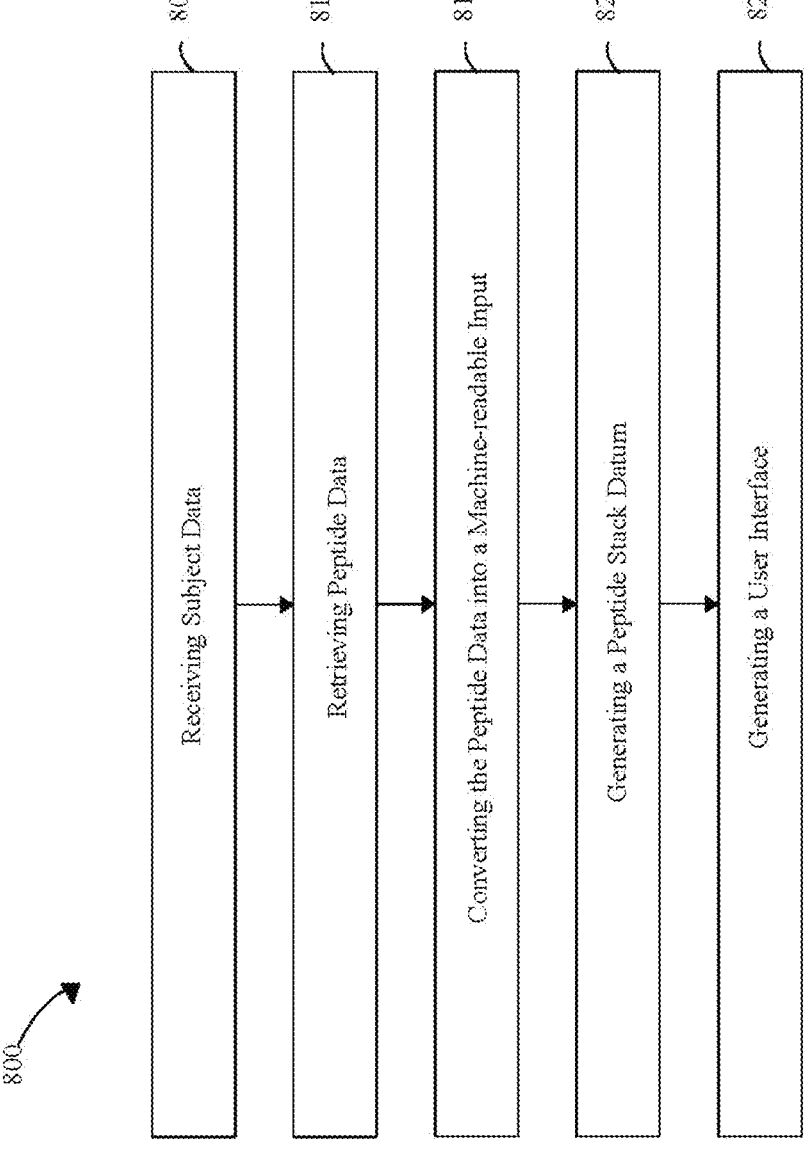
FIG. 8 illustrates a flow diagram of an exemplary method for peptide stack determination.

Referring now to FIG. 8, a flow diagram of an exemplary method 800 for peptide stack determination. Method 800 contains a step 805 of receiving, using at least a processor, subject data, wherein the subject data includes user condition data and a peptide request datum. In some embodiments, receiving the subject data may include training a large language model with a first language training set, wherein the first language training set may include exemplary subject data correlated to exemplary user prompts and generating a user prompt using the trained large language model, wherein the user prompt may be configured to request for additional subject data. In some embodiments, the large language model may be further trained with a second language training set, wherein the second language training set may include interactions of users of different language skills and education levels. In some embodiments, receiving the subject data may include converting the subject data in an audio format into a textual format. These may be implemented as reference to FIGS. 1-7.

With continued reference to FIG. 8, method 800 contains a step 810 of retrieving, using at least a processor, peptide data from a peptide database, wherein the peptide data includes information related to a plurality of peptides. This may be implemented as reference to FIGS. 1-7.

With continued reference to FIG. 8, method 800 contains a step 815 of converting, using at least a processor, peptide data into a machine-readable input. This may be implemented as reference to FIGS. 1-7.

With continued reference to FIG. 8, method 800 contains a step 820 of generating, using at least a processor, a peptide stack datum as a function of subject data and a machine-readable input, wherein the peptide stack datum is related to a combination of at least two peptides of a plurality of peptides that are compatible to user condition data and determining the peptide stack datum includes generating stack training data, wherein the stack training data includes exemplary subject data and exemplary machine-readable inputs correlated to exemplary peptide stack datums, training a stack machine-learning model trained with the stack training data and generating the peptide stack datum using the trained stack machine-learning model. In some embodiments, generating the peptide stack datum may include identifying a target datum from the peptide request datum using a language processing module and determining the at least two peptides for the peptide stack datum as a function of the target datum. In some embodiments, method 800 may further include categorizing, using the at least a processor, the subject data and the peptide stack datum as a function of the target datum and generating, using the at least a processor, a categorized database as a function of the categorized subject data and the peptide stack datum, wherein the categorized database may be accessible by an approved third party. In some embodiments, generating the peptide stack datum may include generating a simulation model and simulating the peptide stack datum using the simulation model to evaluate an effect of the at least two peptides of the peptide stack datum. In some embodiments, generating the peptide stack datum may include updating the stack training data as a function of the simulation, retraining the stack machine-learning model using the updated stack training data and generating the peptide stack datum using the retrained stack machine-learning model. In some embodiments, generating the peptide stack datum may include determining a ratio datum of the at least two peptides of the peptide stack datum as a function of the simulation. In some embodiments, method 800 may further include identifying, using the at least a processor, an outlier datum as a function of the subject data, generating, using the at least a processor, the peptide stack datum as a function of the outlier datum and generating, using the at least a processor, an outlier control datum as a function of the outlier datum. These may be implemented as reference to FIGS. 1-7.

With continued reference to FIG. 8, method 800 contains a step 825 of generating, using at least a processor, a user interface displaying the peptide stack datum on a remote device. These may be implemented as reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
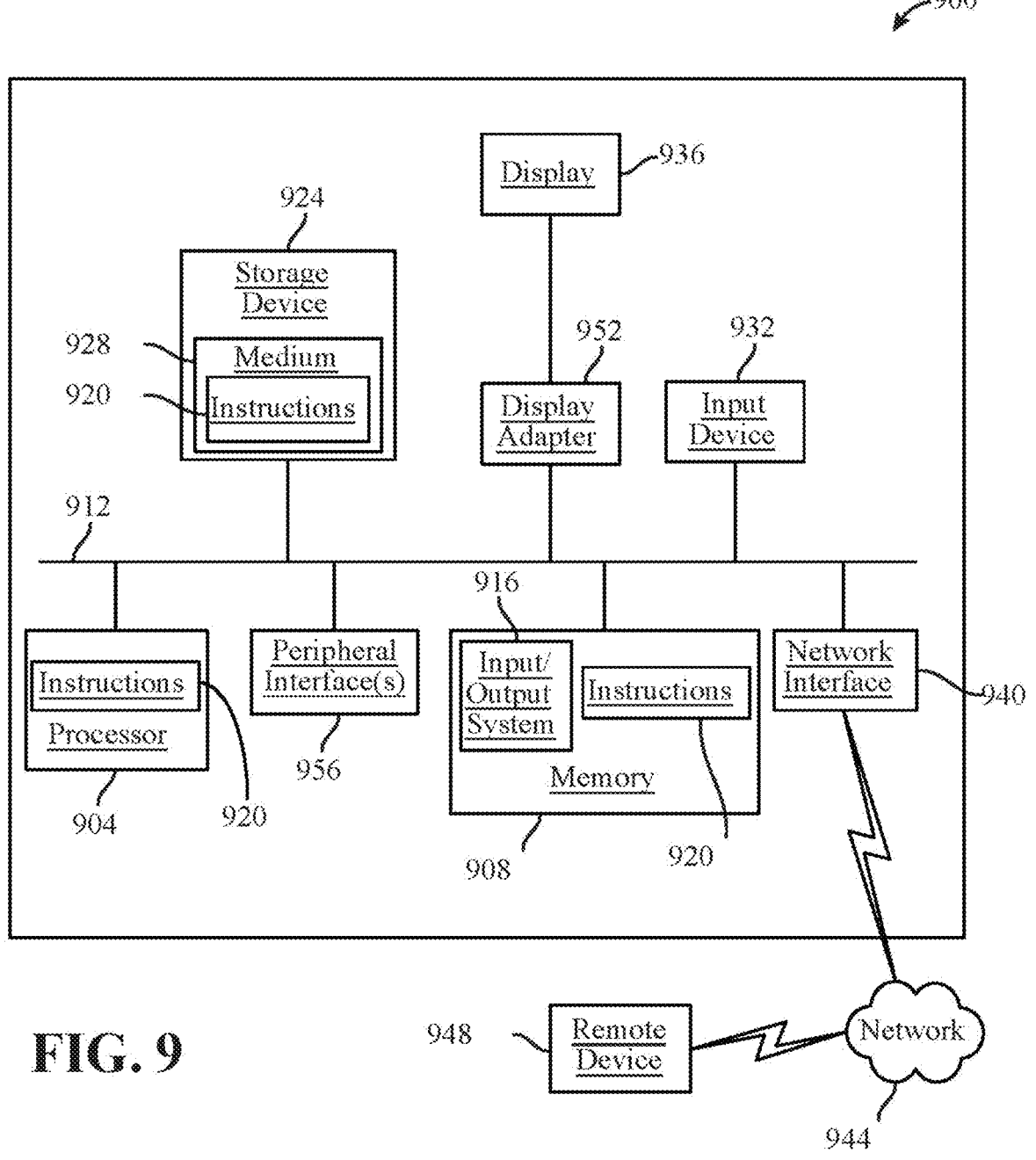
FIG. 9 illustrates a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and memory 908 that communicate with each other, and with other components, via a bus 912. Bus 912 may include any of several types of bus structures including, but not limited to, memory bus, memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIRE-WIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display 936. Examples of a display device include, but are not limited to, a liquid crystal display (LCD), a cathode ray tube (CRT), a plasma display, a light emitting diode (LED) display, and any combinations thereof. Display adapter 952 and display 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for peptide stack determination, the apparatus comprising:
   at least a processor; and
   a memory communicatively connected to the at least a processor, wherein the memory contains instructions configuring the at least a processor to:
   receive subject data, wherein the subject data comprises user condition data and a peptide request datum;
   retrieve peptide data from a peptide database, wherein the peptide data comprises information related to a plurality of peptides;
   convert the peptide data into a machine-readable input;
   generate a peptide stack datum as a function of the subject data and the machine-readable input, wherein the peptide stack datum is related to a combination of at least two peptides of the plurality of peptides that are compatible to the user condition data and determining the peptide stack datum comprises:
   generating stack training data, wherein the stack training data comprises exemplary subject data and exemplary machine-readable inputs correlated to exemplary peptide stack datums;
   training a stack machine-learning model trained with the stack training data; and
   generating the peptide stack datum using the trained stack machine-learning model;
   generating a simulation model;
   simulating the peptide stack datum using the simulation model to evaluate an effect of the at least two peptides of the peptide stack datum, wherein simulating comprises in silico testing, wherein the in silico testing comprises predicting how the at least two peptides of the peptide stack datum interact with each other and with a user's body based on the subject data;
   updating the stack training data as a function of the simulation;
   retraining the stack machine-learning model using the updated stack training data;
   generating the peptide stack datum using the retrained stack machine-learning model; and
   generate a user interface displaying the peptide stack datum on a remote device.

2. The apparatus of claim 1, wherein receiving the subject data comprises:
   training a large language model with a first language training set, wherein the first language training set comprises exemplary subject data correlated to exemplary user prompts; and
   generating a user prompt using the trained large language model, wherein the user prompt is configured to request for additional subject data.

3. The apparatus of claim 2, wherein the large language model is further trained with a second language training set, wherein the second language training set comprises interactions of users of different language skills and education levels.

4. The apparatus of claim 1, wherein receiving the subject data comprises converting the subject data in an audio format into a textual format.

5. The apparatus of claim 1, wherein generating the peptide stack datum comprises:
   identifying a target datum from the peptide request datum using a language processing module; and
   determining the at least two peptides for the peptide stack datum as a function of the target datum.

6. The apparatus of claim 5, wherein the memory contains instructions further configuring the at least a processor to:
   categorize the subject data and the peptide stack datum as a function of the target datum; and
   generate a categorized database as a function of the categorized subject data and the peptide stack datum, wherein the categorized database is accessible by an approved third party.

7. The apparatus of claim 1, wherein generating the peptide stack datum comprises:
   determining a ratio datum of the at least two peptides of the peptide stack datum as a function of the simulation.

8. The apparatus of claim 1, wherein generating the peptide stack datum comprises:
   identify an outlier datum as a function of the subject data;
   generate the peptide stack datum as a function of the outlier datum; and
   generate an outlier control datum as a function of the outlier datum.

9. A method for peptide stack determination, the method comprising:
   receiving, using at least a processor, subject data, wherein the subject data comprises user condition data and a peptide request datum;
   retrieving, using the at least a processor, peptide data from a peptide database, wherein the peptide data comprises information related to a plurality of peptides;
   converting, using the at least a processor, the peptide data into a machine-readable input;
   generating, using the at least a processor, a peptide stack datum as a function of the subject data and the machine-readable input, wherein the peptide stack datum is related to a combination of at least two peptides of the plurality of peptides that are compatible to the user condition data and determining the peptide stack datum comprises:
   generating stack training data, wherein the stack training data comprises exemplary subject data and exemplary machine-readable inputs correlated to exemplary peptide stack datums;
   training a stack machine-learning model trained with the stack training data; and
   generating the peptide stack datum using the trained stack machine-learning model; and
   generating a simulation model;
   simulating the peptide stack datum using the simulation model to evaluate an effect of the at least two peptides of the peptide stack datum, wherein simulating comprises in silico testing, wherein the in silico testing comprises predicting how the at least two peptides of the peptide stack datum interact with each other and with a user's body based on the subject data;
   updating the stack training data as a function of the simulation;

retraining the stack machine-learning model using the updated stack training data;

generating the peptide stack datum using the retrained stack machine-learning model; and generating, using the at least a processor, a user interface displaying the peptide stack datum on a remote device.

10. The method of claim 9, wherein receiving the subject data comprises:

training a large language model with a first language training set, wherein the first language training set comprises exemplary subject data correlated to exemplary user prompts; and generating a user prompt using the trained large language model, wherein the user prompt is configured to request for additional subject data.

11. The method of claim 10, wherein the large language model is further trained with a second language training set, wherein the second language training set comprises interactions of users of different language skills and education levels.

12. The method of claim 9, wherein receiving the subject data comprises converting the subject data in an audio format into a textual format.

13. The method of claim 9, wherein generating the peptide stack datum comprises:

identifying a target datum from the peptide request datum using a language processing module; and determining the at least two peptides for the peptide stack datum as a function of the target datum.

14. The method of claim 13, further comprising:

categorizing, using the at least a processor, the subject data and the peptide stack datum as a function of the target datum; and generating, using the at least a processor, a categorized database as a function of the categorized subject data and the peptide stack datum, wherein the categorized database is accessible by an approved third party.

15. The method of claim 9, wherein generating the peptide stack datum comprises:

determining a ratio datum of the at least two peptides of the peptide stack datum as a function of the simulation.

16. The method of claim 9, wherein generating the peptide stack datum comprises:

identifying, using the at least a processor, an outlier datum as a function of the subject data;

generating, using the at least a processor, the peptide stack datum as a function of the outlier datum; and generating, using the at least a processor, an outlier control datum as a function of the outlier datum.

* * * * *